(12) United States Patent
Fuller et al.

(10) Patent No.: US 8,337,412 B2
(45) Date of Patent: Dec. 25, 2012

(54) INTEGRAL FLUID REGULATOR FOR ENDOSCOPIC VESSEL DISSECTION/HARVESTING DEVICE

(75) Inventors: Kay L. Fuller, Ann Arbor, MI (US); Randal J. Kadykowski, South Lyon, MI (US)

(73) Assignees: Terumo Cardiovascular Systems Corporation, Ann Arbor, MI (US); Olympus Medical Systems Corporation, Tokyo (JP)

( * ) Notice: Subject to any disclaimer, the term of this patent is extended or adjusted under 35 U.S.C. 154(b) by 1213 days.

(21) Appl. No.: 11/998,692

(22) Filed: Nov. 29, 2007

(65) Prior Publication Data

US 2009/0139531 A1    Jun. 4, 2009

(51) Int. Cl.
*A61B 5/00* (2006.01)
*A61B 10/00* (2006.01)

(52) U.S. Cl. .................................. 600/561; 600/562

(58) Field of Classification Search .......... 600/560–572, 600/101, 104, 109, 114–116, 121–125
See application file for complete search history.

(56) References Cited

U.S. PATENT DOCUMENTS

| | | | |
|---|---|---|---|
| 4,425,915 A | 1/1984 | Ivanov | |
| 4,478,220 A | 10/1984 | Di Giovanni et al. | |
| 4,491,133 A | 1/1985 | Menges et al. | |
| 5,445,167 A | 8/1995 | Yoon et al. | |
| 5,474,567 A | 12/1995 | Stefanchik et al. | |
| 5,575,759 A * | 11/1996 | Moll et al. | 600/207 |
| 5,601,573 A | 2/1997 | Fogelberg et al. | |
| 5,601,574 A | 2/1997 | Stefanchik et al. | |
| 5,681,330 A | 10/1997 | Hughett et al. | |
| 5,833,700 A | 11/1998 | Fogelberg et al. | |
| 6,162,236 A | 12/2000 | Osada | |
| 6,638,297 B1 | 10/2003 | Huitema | |
| 6,964,363 B2 | 11/2005 | Wales et al. | |
| 6,989,003 B2 * | 1/2006 | Wing et al. | 604/161 |
| 7,059,508 B2 | 6/2006 | Shelton, IV et al. | |
| 7,063,699 B2 | 6/2006 | Hess et al. | |
| 7,070,602 B2 | 7/2006 | Smith et al. | |
| 7,077,803 B2 | 7/2006 | Kasahara et al. | |
| 7,105,000 B2 | 9/2006 | McBrayer | |
| 7,449,011 B2 * | 11/2008 | Wenchell et al. | 604/164.01 |
| 7,507,209 B2 * | 3/2009 | Nezhat et al. | 600/560 |
| 2005/0149094 A1 | 7/2005 | Kasahara et al. | |
| 2005/0159764 A1 | 7/2005 | Kasahara et al. | |
| 2006/0079921 A1 * | 4/2006 | Nezhat et al. | 606/185 |

* cited by examiner

*Primary Examiner* — Jeffrey G Hoekstra
(74) *Attorney, Agent, or Firm* — Gael Diane Tisack; Darryl Newell; MacMillan, Sobanski & Todd, LLC

(57) ABSTRACT

A device for dissecting and/or harvesting a vessel includes an integrally adjustable insufflation device to supply an insufflation fluid to a subcutaneous area within a patient. The integrally adjustable insufflation device includes one or more one fluid control mechanisms to regulate the pressure rate and/or flow rate of the insufflation fluid being supplied to the subcutaneous area from within a sterile field surrounding the subcutaneous area.

18 Claims, 2 Drawing Sheets

INTEGRAL FLUID REGULATOR FOR ENDOSCOPIC VESSEL DISSECTION/HARVESTING DEVICE

CROSS-REFERENCE TO RELATED APPLICATIONS AND STATEMENT REGARDING SPONSORED RESEARCH

Not applicable.

BACKGROUND OF THE INVENTION

The present invention relates to the harvesting of blood vessels and, more particularly, to a method and apparatus for dissection and removal of sections of blood vessels.

The harvested vessels are used in many surgical procedures, including use as a coronary artery bypass graft, or in other cardiovascular procedures. As one example, in vascular and cardiovascular procedures, a blood vessel or vessel section, such as an artery or vein, is "harvested" (i.e., removed) from its natural location in a patient's body and is used elsewhere in the body. In coronary artery bypass grafting surgery, for example, the harvested blood vessel is used to form a bypass between an arterial blood source and the coronary artery that is to be bypassed. Among the preferred sources for the vessels to be used as the bypass graft are the saphenous vein in the leg and the radial artery in the arm.

In the past, the harvesting was done through a continuous incision (e.g., along the leg) that exposed the full length of the desired vein section. The continuous incision had been necessary in order to provide adequate exposure for visualizing the vein and for introducing the surgical instruments to sever, cauterize and ligate the tissue and side branches of the vessel.

A more recent development has been a minimally-invasive technique that employs a small incision for locating the desired vessel and for introducing one or more endoscopic devices into the small incision. Commercially available endoscopic products for performing the blood vessel harvesting procedure include a number of separate devices that are used for each stage of the dissecting and harvesting of the vessel. These separate endoscopic devices, are in turn, connected to remote or outside pieces of equipment that are used to control the endoscopic devices. In many instances, an endoscope having a camera and light cable is used in order to visualize both the dissection and harvesting procedures. Also, the harvester devices and/or dissector devices have electrical or other lines attached in order to supply the dissecting and/or cauterizing of the vessel.

The harvesting of blood vessels also includes the use of insufflators in order to create an open area around the vessel being dissected and harvested. The insufflators are attached to supplies of air or $CO_2$ that are connected to external sources in the operating room. The currently available insufflators are typically intended for use in general and gynecological endoscopic surgeries, and have historically performed safely when used as intended. Such insufflators are commonly utilized in both day surgery and hospital operating rooms. Many types of endoscopic surgical procedures that include the use of insufflators typically require several liters of $CO_2$ to inflate and maintain the area surrounding the surgical site. As such, the currently marketed insufflators typically have pressure/flow rates ranging from about 0.1 liters/min to about 20.0± liters/min. These insufflators are particularly designed to deliver $CO_2$ into the endoscopic surgical field at high flow rates ranging between about 8-20 liters/min.

In certain instances, however, there may be a concern that excessive gas (e.g., $CO_2$) pressure and/or flow rates may be introduced into the subcutaneous area during an endoscopic vessel dissection/harvesting procedure. The clinician is particularly careful to prevent or reduce any risk that the vessel harvesting procedure could induce a gas embolism(s). This is a concern since the clinician is often not able to quickly and independently set or adjust the pressure rates and/or flow rates. This becomes a concern since the clinician is within the sterile field while any means for adjusting the insufflators is remote from the sterile field. Typically, the insufflator flow rate settings are controlled from outside the sterile field by a circulating assistant who must then respond to verbal directions from the clinician, rather than by the clinician located within the sterile field.

There is a particular concern when the endoscopic procedure is an endoscopic vessel harvesting procedure since such procedures require much lower $CO_2$ pressure rates and/or flow rates than general and gynecological endoscopy procedures, as noted above. These lower flow rates, which typically range between 0.5 liters/min to 5.0 liters/min, are needed in order to achieve and maintain the precise inflation of the subcutaneous areas that are needed during the vessel dissection and harvesting.

It would be desirable to have an insufflator device that provides a rapid and easily accessible system for adjusting the insufflation gases being used in endoscopic procedures.

SUMMARY OF THE INVENTION

In one aspect, there is provided an integral fluid-regulating endoscopic device for dissecting and/or harvesting a vessel from a body. The integral fluid-regulating endoscopic device includes a sheath that is at least partially inserted in a body through a cut skin portion. The sheath is used for one or more of: i) forming a subcutaneous area in the body at least partially around the vessel, ii) dissecting the vessel from the body, and iii) harvesting the vessel from the body.

The integral fluid-regulating endoscopic device also includes an integrally adjustable insufflation device that supplies an insufflation fluid to the subcutaneous area. The integrally adjustable insufflation device includes at least one fluid control mechanism to regulate the pressure and/or flow rate of the insufflation fluid being supplied to the subcutaneous area. The fluid control mechanism is adjustable by a clinician who is using the integral fluid-regulating endoscopic device. The integrally adjustable insufflation device can deliver one or more insufflation fluids, such as, for example, one or more gases or liquids.

In certain embodiments, the integrally adjustable insufflation device can include an internal fluid control mechanism and an external fluid control mechanism. The internal fluid control mechanism and the external fluid control mechanism are configured to be within a sterile field surrounding the cut skin portion of the body. At least one fluid control mechanism can be positioned at a proximal end of the sheath.

Also, in certain embodiments, the integrally adjustable insufflation device can include a one-way valve positioned at a distal end of the sheath. The one-way fluid control valve allows the insufflation fluid to exit from the integrally adjustable insufflation device, but prevents debris from entering the integrally adjustable insufflation device.

In a further and/or alternative aspect of the present invention, the integral fluid-regulating endoscopic device can further include one or more of an imaging system, a dissecting device and a harvesting device.

Various objects and advantages of this invention will become apparent to those skilled in the art from the following detailed description of the preferred embodiment, when read in light of the accompanying drawings.

DETAILED DESCRIPTION OF THE PREFERRED EMBODIMENT

Figure 1:
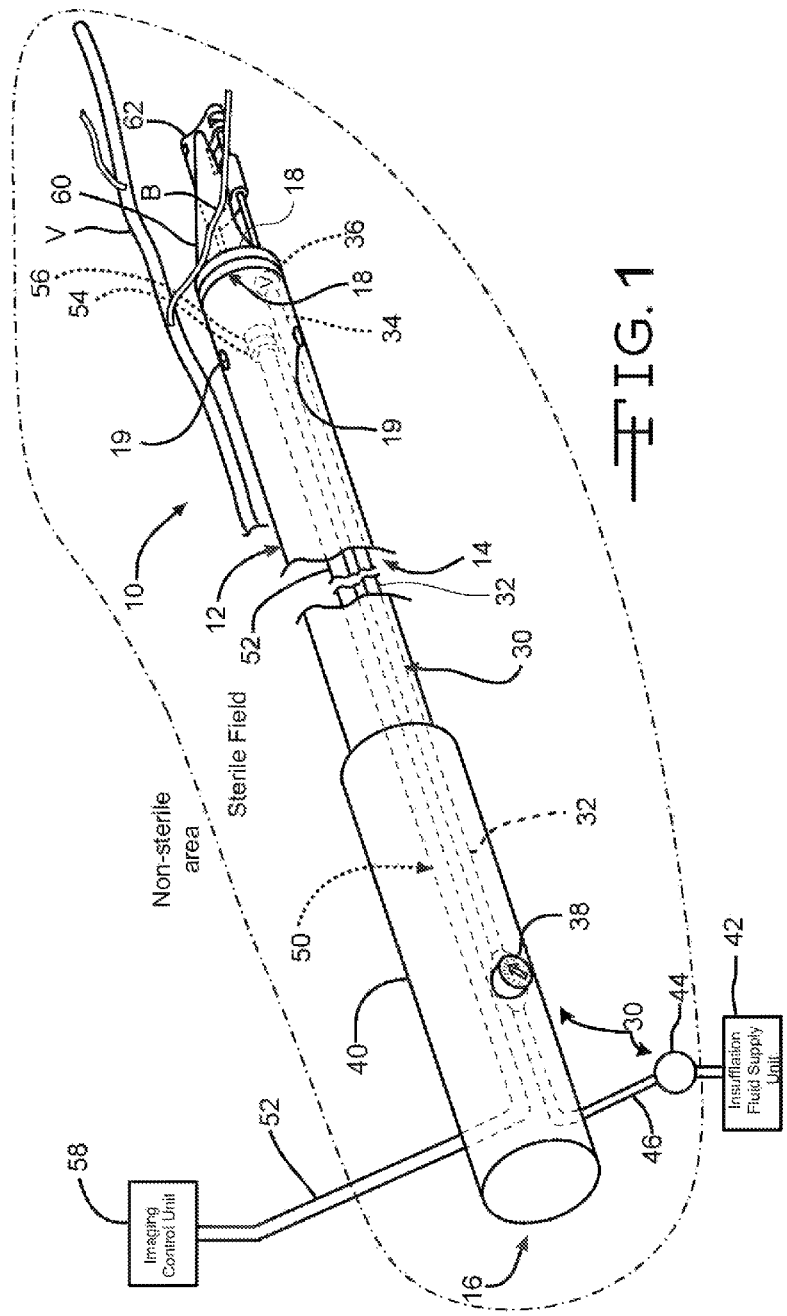
FIG. 1 is a structure diagram, partially in phantom, showing an endoscopic device having an integrally adjustable insufflation device 30.

FIG. 1 is a structure diagram of one embodiment of an integral fluid-regulating endoscopic device 10 for dissecting and/or harvesting a vessel V and for severing branches B from the vessel.

It is to be understood that the integral fluid-regulating endoscopic device 10 can be used to regulate any desired fluids, including such non-limiting examples as gases, such as $CO_2$, and liquids, such as water. For ease of discussion herein, the integral fluid-regulating endoscopic device 10 will be described herein as regulating an insufflation gas, as will be further explained below.

The integral fluid-regulating endoscopic device 10 eliminates the need for any external, or peripheral, control of the fluid pressure and/or flow rates by someone other than the clinician using the integral fluid-regulating endoscopic device 10.

The integral fluid-regulating endoscopic device 10 also allows the clinician to quickly adjust, and thereby regulate, the fluid pressure and/or flow rates from within the sterile field.

In one non-limiting embodiment, the integral fluid-regulating endoscopic device 10 includes an elongated sheath 12 that is at least partially inserted subcutaneously in a body through a cut skin portion. The sheath 12 defines an inner space 14 and has a proximal end 16 and a distal end 18.

In certain embodiments, the insufflation gas is discharged from the distal end 18 into the subcutaneous area in the body. In other embodiments, the sheath 12 can include one or more discharge ports or holes 19 that are in fluid communication with the inner space 14. The insufflation gas escaping from the distal end 18 and/or ports 19 enters the subcutaneous area around the vessel and keeps the surrounding tissue away from the endoscopic device 10.

In order to rapidly and accurately regulate the pressure and/or flow rates of the insufflation gas, the integral fluid-regulating endoscopic device 10 includes an integrally adjustable insufflation device 30. While insufflation devices have been used in the dissection and harvesting of blood vessels, until now there has not been an endoscopic device that allows a clinician to regulate the pressure and/or flow rate of the insufflation gas from within a sterile field surrounding the cut skin portion of the body.

The amount and the pressure of insufflation gas that are needed to inflate the area surrounding the vessel to be harvested can vary, depending on the patient's body configuration and the types of obstacles (for example, fat, connective tissues, blood vessel, and the like) that the clinician encounters during the dissecting and harvesting procedures. The clinician may need to act, or react, quickly as circumstances change during these procedures. It is therefore desirable that the clinician be able to quickly and effectively control the both pressure and the flow rates immediately upon encountering any obstacles during the dissecting and harvesting procedures.

The integrally adjustable insufflation device 30 prevents any excessively high pressure and excessively fast flow rates of insufflation gas from exiting the endoscopic device 10. The integrally adjustable insufflation device 30 ensures that the pressure and/or flow rates of gas entering (and ultimately exiting) the inner space 14 of the endoscopic device 10 are adequate, but not excessive. In certain embodiments, the integrally adjustable insufflation device 30 can provide a "step-down" of the pressure and/or the amount of insufflation gas exiting from the inner space 14, while simultaneously allowing a substantially continuous flow of the insufflation gas into the subcutaneous area. It is to be understood that, in certain embodiments, the integrally adjustable insufflation device 30 can adjust the pressure and the flow rate simultaneously, or can adjust the pressure and the flow rate in a sequential manner. This adjustability feature of the integrally adjustable insufflation device 30 provides an especially useful integral fluid-regulating endoscopic device 10 that can be readily manipulated by the clinician, while still remaining within the sterile field. In particular, the ability for the clinician to control the supply of a low pressurized insufflation gas to the subcutaneous area adds a degree of control to the dissection and harvesting procedures that had not been previously available.

In the embodiment shown herein, the integrally adjustable insufflation device 30 includes a supply line 32 that is axially positioned within the inner space 14 of the sheath 12. The supply line 32 has a discharge end 34 that is located near the distal end 18 of the sheath 12. The supply line 32 allows the insufflation gas to be delivered to the subcutaneous area either via the radially extending openings 19 in the distal end 18 of the sheath 12 or directly through the distal end 18.

In certain embodiments, the integrally adjustable insufflation device 30 includes a one-way fluid control valve 36. The one-way fluid control valve 36 is fluidly and operatively connected to the supply line 32 and can be positioned at the discharge end 34. In certain embodiments, the one-way fluid valve 36 is positioned adjacent to the distal end 18 of the sheath 12.

The one-way fluid control valve 36 allows the insufflation gas to pass from the supply line 32, but prevents debris from entering the supply line 32.

The integrally adjustable insufflation device 30 includes one or more fluid control mechanisms 38 that configured to regulate at least one of a pressure and flow rate of the insufflation gas being supplied to the subcutaneous area. In the embodiment shown in FIG. 1, at least one fluid control mechanism is designated as an internal fluid control mechanism 38 and at least one other fluid control mechanism is designated as an external fluid control mechanism 44, as further described below. As shown in FIG. 1, the internal fluid control mechanism 38 is operatively connected to the supply line 32. The internal fluid control mechanism 38 is configured to control the pressure and/or the flow rates of the insufflation gas being discharged from the supply line 32 via the one-way control valve 36.

In certain embodiments, the internal fluid control mechanism 38 can be either a one-way valve or a pressure relief type regulator that acts as a "high-pressure/flow step-down" mechanism. In certain other embodiments, the internal fluid control mechanism 38 can include a precision pressure/flow rate gauging, or setting, mechanism. It is to be understood that other suitable mechanisms can be used that allow the clinician to also infinitely vary the pressure and/or flow rates of the insufflation gas being delivered through the supply line 32 to the subcutaneous area surrounding the vessel.

In one embodiment, as shown in FIG. 1, the internal fluid control mechanism 38 is incorporated into a handle 40 of the integral fluid-regulating endoscopic device 10. The internal fluid control mechanism 38 is also operatively connected to a fluid supply 42.

Thus, the integral fluid-regulating endoscopic device 10 allows for a clinician-controlled and immediately responsive adjustment of the gas pressure and/or flow rate entering the subcutaneous area.

It is also within the contemplated scope of the present system that, in certain embodiments, the integrally adjustable insufflation device 30 can include both the internal fluid control mechanism 38 and an external fluid control mechanism 44. As shown in FIG. 1, the additional, or external fluid control mechanism 44 can be connected to the handle 40 of the endoscopic device 10 by a suitable external supply line 46. The external supply line 46 has a desired length such that the external fluid control mechanism 44 substantially remains within the sterile field and within easy reach by the clinician.

Thus, the integrally adjustable insufflation device 30 allows the integral fluid-regulating endoscopic device 10 to be regulated proximally, distally, or both proximally and distally. The adjustable pressure/flow rates of the integrally adjustable insufflation device 30 can be preset for specific pressure/flow rates, be varied for substantially instantaneous control of the pressure/flow rates, and can further have a combination of these features. The clinician can thereby control the desired flow/pressure rates directly at the device handle, rather than via a remote insufflator monitor.

In certain embodiments, the integral fluid-regulating endoscopic device 10 can include one or more instruments with which to dissect and harvest the vessels. In one non-limiting example, the integral fluid-regulating endoscopic device 10 can include an imaging system 50 that is axially positioned within the inner space 14 of the sheath 12. The imaging system 50 can, for example, include a power supply 52, an image-receiving device 54 and a light source 56. In certain embodiments, the power supply 52 can be remotely controlled to be in an "on" or illuminating mode, or in an "off" or non-illuminating mode. The image-receiving device 54 can convert images into signals for transmission, recording and/or storage, and/or takes photographs of such images. In many embodiments, the image-receiving device 54 is a camera-type device. The imaging system 50 can be operatively connected to a control unit 58 where an image captured by the image-receiving device 54 can be displayed, recorded and/or printed.

In certain embodiments, the integral fluid-regulating endoscopic device 10 can also include a dissecting tool 60 and/or a harvesting tool 62. It is to be understood that various types of suitable dissecting tools 60 and harvesting tools 62 are contemplated as being useful, and that such various types are within the scope of the present invention. It is to be understood that the harvesting tool 62 can be situated in a separate device from the dissector tool 60; however, for ease of illustration herein, both the dissecting tool 60 and the harvesting tool 62 are shown in the same integral fluid-regulating endoscopic device 10.

To begin the dissecting and harvesting procedure using the integral fluid-regulating endoscopic device 10, the integrally adjustable insufflation device 30 is engaged to deliver a desired supply of the insufflation gas into the subcutaneous area at a desired pressure and rate of flow. As the dissecting step is progressing, the clinician is able to regulate the pressure and flow rates, as described above. Once the vessel is dissected from the surrounding tissue, the clinician then begins the harvesting step of the procedure. Similarly, as the harvesting procedure is progressing, the clinician is able to regulate the pressure and flow rates, as described above.

Figure 2:
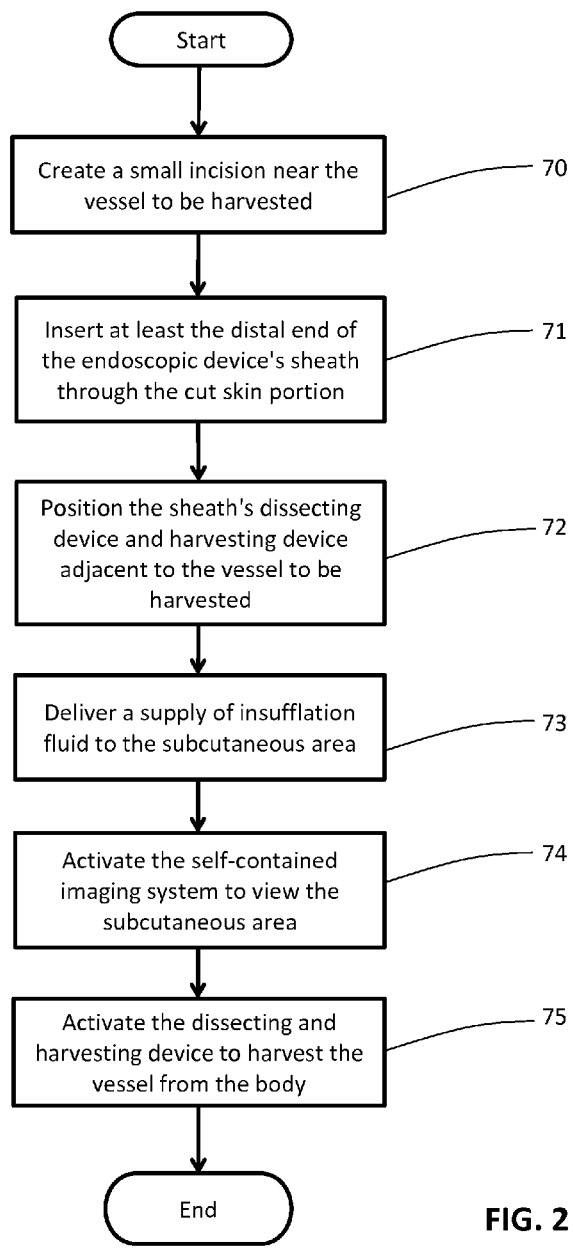
FIG. 2 is a flowchart showing a method of performing a minimally-invasive vein harvesting procedure using the integral fluid-regulating endoscopic device.

Referring now to FIG. 2, the flowchart describes the basic steps of a minimally-invasive vein harvesting procedure. The minimally-invasive vein harvesting procedure begins in step 70 by creating a small incision in the appropriate body area for the specific target vessel. In step 71, the endoscopic device is inserted through the incision, and in step 72 it is positioned adjacent to the target vessel in preparation for dissection and harvesting.

Insufflation fluid is introduced through the endoscopic device to the subcutaneous area in step 73 of FIG. 2. Once the insufflation fluid has created the proper open subcutaneous area around the target vessel, the endoscopic imaging system is then activated in step 74. Since the clinician can now visualize the subcutaneous area around the vessel, the dissection and harvesting of the target vessel can begin in step 75.

While the invention has been described with reference to various and preferred embodiments, it should be understood by those skilled in the art that various changes may be made and equivalents may be substituted for elements thereof without departing from the essential scope of the invention. In addition, many modifications may be made to adapt a particular situation or material to the teachings of the invention without departing from the essential scope thereof. Therefore, it is intended that the invention not be limited to the particular embodiment disclosed herein contemplated for carrying out this invention, but that the invention will include all embodiments falling within the scope of the claims.

What is claimed is:

1. An integral fluid-regulating endoscopic device for dissecting and/or harvesting a vessel from a body comprising:
   a sheath configured to be at least partially inserted in a body through a cut skin portion and configured for one or more of: i) forming a subcutaneous area in the body at least partially around the vessel, ii) dissecting the vessel from the body, and iii) harvesting the vessel from the body;
   an integrally adjustable insufflation device configured to supply an insufflation fluid to the subcutaneous area; the integrally adjustable insufflation device including one or more fluid control mechanisms configured to regulate at least one of a pressure and flow rate of the insufflation fluid being supplied to the subcutaneous area from within a sterile field surrounding the cut skin portion of the body.

2. The device of claim 1, wherein at least one fluid control mechanism is positioned at a proximal end of the sheath.

3. The device of claim 1, wherein the fluid control mechanism includes an internal fluid control mechanism and an external fluid control mechanism.

4. The device of claim 3, wherein the internal fluid control mechanism and the external fluid control mechanism are configured to be within the sterile field surrounding the cut skin portion of the body.

5. The device of claim 1, wherein the integrally adjustable insufflation device includes a one-way valve positioned adjacent to a distal end of the sheath.

6. The device of claim 5, wherein the one-way fluid control valve is configured to allow the insufflation fluid to exit from the integrally adjustable insufflation device, but prevents debris from entering the integrally adjustable insufflation device.

7. The device of claim 1, further including one or more of an imaging system, a dissecting device and a harvesting device.

8. The device of claim 1, wherein the integrally adjustable insufflation device includes:
   a supply line axially positioned within an inner space of the sheath, the supply line having a discharge end located near a distal end of the sheath, the supply line being configured to allow the insufflation fluid to be delivered to the subcutaneous area;
   a one-way fluid control valve connected to the supply line and configured to allow the insufflation fluid to pass from the supply line, but prevent debris from entering the supply line; and
   at least one internal fluid control mechanism connected to the supply line.

9. A method of dissecting a vessel from a body using an integral fluid-regulating endoscopic device for dissecting and/or harvesting a vessel from a body, wherein the endoscopic device includes a sheath configured to be at least partially inserted in a body through a cut skin portion and configured for one or more of: i) forming a subcutaneous area in the body at least partially around the vessel, ii) dissecting the vessel from the body, and iii) harvesting the vessel from the body, and the endoscopic device further includes an integrally adjustable insufflation device configured to supply an insufflation fluid to the subcutaneous area, wherein the integrally adjustable insufflation device includes one or more fluid control mechanisms configured to regulate, from within a sterile field surrounding the cut skin portion of the body, at least one of a pressure and flow rate of the insufflation fluid being supplied to the subcutaneous area, the method comprising the steps of:
   inserting at least a distal end of the sheath into the body alongside the vessel to form a subcutaneous area substantially surrounding the vessel; and
   delivering a supply of insufflation fluid to the subcutaneous area in an amount sufficient to at least partially insufflate the subcutaneous area, wherein the insufflation fluid pressure and/or flow rate is adjustable from within a sterile field surrounding the subcutaneous area by a clinician who is using the integral fluid-regulating endoscopic device.

10. The method of claim 9, wherein at least one fluid control mechanism is positioned at a proximal end of the sheath.

11. The method of claim 9, wherein the fluid control mechanism includes an internal fluid control mechanism and an external fluid control mechanism.

12. The method of claim 11, wherein the internal fluid control mechanism and the external fluid control mechanism are configured to be within a sterile field surrounding the cut skin portion of the body.

13. The method of claim 9, wherein the integrally adjustable insufflation device includes a one-way valve positioned adjacent to a distal end of the sheath.

14. The method of claim 13, wherein the one-way fluid control valve is configured to allow the insufflation fluid to exit from the integrally adjustable insufflation device, but prevents debris from entering the integrally adjustable insufflation device.

15. The method of claim 9, wherein the clinician-controlled integral fluid-regulating endoscopic device further includes one or more of an imaging system; a dissecting device and a harvesting device.

16. The method of claim 15, wherein the method further includes one or more of:
   activating the self-contained imaging system to view at least a portion of the subcutaneous area;
   positioning the dissecting device and the harvesting device to a position adjacent to the vessel; and
   activating the dissecting device and the harvesting device whereby the vessel is harvested from the body.

17. An integral fluid-regulating endoscopic device for dissecting and/or harvesting a vessel from a body comprising:
   a sheath with proximal and distal ends, wherein the distal end is at least partially inserted in a body through a cut skin portion and configured for one or more of: i) forming a subcutaneous area in the body at least partially around the vessel, ii) dissecting the vessel from the body, and iii) harvesting the vessel from the body;
   a handle disposed at the proximal end of the sheath;
   an insufflation passage extending from the handle towards the distal end of the sheath; and
   at least one insufflation fluid-regulating device coupled to the insufflation passage, delivering a supply of insufflation fluid to the subcutaneous area in an amount sufficient to at least partially insufflate the subcutaneous area, wherein the insufflation fluid pressure and/or flow rate is adjustable from within a sterile field surrounding the subcutaneous area by a clinician who is using the integral fluid-regulating endoscopic device.

18. The device of claim 17, wherein at least one insufflation fluid-regulating device is located on the handle.

* * * * *